(12) United States Patent
Norman et al.

(10) Patent No.: US 8,921,608 B2
(45) Date of Patent: *Dec. 30, 2014

(54) CATALYST AND METHOD HAVING SELECTIVITY TO ISOBUTYRALDEHYDE VIA CATALYST INDUCTION

(71) Applicant: Eastman Chemical Company, Kingsport, TN (US)

(72) Inventors: David William Norman, Kingsport, TN (US); Elaine Beatrice Mackenzie, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 68 days.

This patent is subject to a terminal disclaimer.

(21) Appl. No.: 13/837,694

(22) Filed: Mar. 15, 2013

(65) Prior Publication Data
US 2013/0324713 A1 Dec. 5, 2013

Related U.S. Application Data

(60) Provisional application No. 61/653,677, filed on May 31, 2012.

(51) Int. Cl.
*C07C 45/50* (2006.01)
*B01J 31/24* (2006.01)

(52) U.S. Cl.
CPC .......... *C07C 45/505* (2013.01); *B01J 31/2447* (2013.01); *C07C 45/50* (2013.01)
USPC ........................... 568/454; 568/455; 540/145

(58) Field of Classification Search
CPC . C07C 45/505; C07D 487/22; B07J 31/2447; B07J 2231/321; B07J 2231/822; B07J 31/24
USPC .................................. 568/454, 455; 540/145
See application file for complete search history.

(56) References Cited

U.S. PATENT DOCUMENTS 5,817,884 A 10/1998 Bahrmann

FOREIGN PATENT DOCUMENTS

| EP | 1 478 439 A1 | 11/2004 |
| EP | 1 886 680 A1 | 2/2008 |
| WO | WO 2008/094222 A2 | 8/2008 |

OTHER PUBLICATIONS

Adler, Alan D. et al.; "On the Prepartation of Metalloporphyrins"; J. inorg. nucl. Chem., vol. 32; 1970; pp. 2443-2445.
Bowen, Richard J. et al.; "Convenient Synthetic Routes to Bidentate and Monodentate 2-, 3- and 4-pyridyl Phosphines: Potentially Useful Ligands for Water-Soluble Complex Catalysts"; Journal of Organometallic Chemistry, vol. 554; 1998; pp. 181-184.
Kamer, Paul C. J. et al.; "Chapter 3 Rhodium Phosphite Catalysts"; Rhodium Catalyzed Hydroformylation; 2000; pp. 35-62.
Kleij, Arjan W. et al.; "Encapsulated Transition Metal Catalysts Comprising Peripheral Zn(II)salen Building Blocks: Template-Controlled Reactivity and Selectivity in Hydroformylation Caralysis"; The Royal Society of Chemistry Communication; 2005; pp. 3661-3663.
Kleij, Arjan W. and Reek, Joost N. H.; "Ligand-Template Directed Assembly: An Efficient Approach for the Supramolecular Encapsulation of Transition-Metal Catalysts"; Chem. Eur. J., vol. 12; 2006; pp. 4218-4227.
Kleij, Arjan W. et al.; "$Zn^{II}$—Salphen Complexes as Versatile Building Blocks for the Construction of Supramolecular Box Assemblies"; Chem. Eur. J, vol. 11; 2005; pp. 4743-4750.
Kleij, Arjan W. et al.; "Template-Assisted Ligand Encapsulation; the Impact of an Unusal Coordination Geometry on a Supramolecular Pyridylphosphine-Zn(II)porphyrin Assembly"; Inorganic Chemistry Communication, vol. 44, No. 22; 2005; pp. 7696-7698.
Kuil, Mark et al.; "High-Precision Catalysts: Regioselective Hydroformylation of Internal Alkenes by Encapsulated Rhodium Complexes": Journal of American Chemical Society, vol. 128; 2006; pp. 11344-11345.
Meyer, W. H. et al.; "Tri (3-pyridyl) Phosphine as amphiphilic ligand in rhodium-catalysed hydroformylation of 1-hexene"; Z. Naturforsch, vol. 62b; 2007; pp. 339-345.
Slagt, Vincent F. et al.; "Assembly of Encapsulated Transition Metal Catalysts"; Angew. Chem. Int. Ed., vol. 40, No. 22; 2001; pp. 4271-4274.
Slagt, Vincent F. et al.; "Encapsulation of Transition Metal Catalysts by Ligand-Template Directed Assembly"; Journal American Chemical Society, vol. 126; 2004; pp. 1526-1536.
Slagt, Vincent et al.; "Fine-Tuning Ligands for Catalysts Using Supramolecular Strategies"; European Journal of Inorganic Chemistry; 2007; pp. 4653-4662.
Van Leeuwen, Piet W. N. M.; "Chapter 1 Introduction to Hydroformylation, Phosphorus Ligands in Homogeneous Catalysts"; Rhodium Catalyzed Hydroformylation; 2000; pp. 1-8.
Van Leeuwen, Piet W. N. M. et al.; "Chapter 4 Phosphines as Ligands, Bite Angle Effects for Diphosphines"; Rhodium Catalyzed Hydroformylation: 2000; pp. 63-105.
Wajda-Hermanowicz, K. et al.; "Rhodium carbonyl complexes of the trans-[RhCl(CO)(PE3)] tyoe with psyridylphosphines"; Transition Met. Chem., vol. 13: 1988; 101-103.
Co-pending U.S. Appl. No. 13/484,979, filed May 31, 2012; Norman et al.
Co-pending U.S. Appl. No. 13/485,033, filed May 31, 2012; Norman et al.
Non-Final Office Action notification date Jul. 16, 2013 received in co-pending U.S. Appl. No. 13/485,033.

(Continued)

*Primary Examiner* — Sikarl Witherspoon
(74) *Attorney, Agent, or Firm* — William K. McGreevey

(57) ABSTRACT

Industrially relevant product selectivities and reaction rates are obtained from rhodium catalyzed hydroformylation of propylene via the use of a novel induction period in which the supramolecular ligand assembly, the rhodium precatalyst and an initial substrate are allowed to form a hydroformylation catalyst that is more selective toward branched aldehydes. Upon heating this incubated mixture and addition of propylene, iso-butyraldehyde is obtained in higher concentrations and rates that are otherwise unattainable.

16 Claims, No Drawings

(56) References Cited

OTHER PUBLICATIONS

Non-Final Office Action notification date Jul. 17, 2013 received in co-pending U.S. Appl. No. 13/484,979.

Notification of Transmittal of the International Search Report and the Written Opinion of the International Searching Authority, or the Declartion date of mailing Sep. 15, 2013 received in corresponding International Application No. PCT/US2013/042986.

Notification of Transmittal of the International Search Report and the Written Opinion of the International Searching Authority, or the Declaration date of mailing Sep. 16, 2013 received in corresponding International Patent Application No. PCT/US2013/042989.

Notification of Transmittal of the International Search Report and the Written Opinion of the International Searching Authority, or the Declaration date of mailing Sep. 16, 2013 received in corresponding International Patent Application No. PCT/US2013/042992.

CATALYST AND METHOD HAVING SELECTIVITY TO ISOBUTYRALDEHYDE VIA CATALYST INDUCTION

CROSS-REFERENCE TO RELATED APPLICATION

This application claims priority to U.S. Provisional Application No. 61/653,677 filed May 31, 2012, the disclosure of which is incorporated herein by reference in its entirety.

BACKGROUND OF THE INVENTION

Iso-butyraldehyde derivatives are useful solvents and co-monomers in high performance polyesters; however, increasing demands for these materials have created unprecedented challenges for global iso-butyraldehyde production. Hydroformylation, the addition of hydrogen ($H_2$) and carbon monoxide (CO), mixtures of which are known as syngas, to an unsaturated bond is used to produce iso-butyraldehyde from propylene. This process provides a mixture of the linear product, normal-butyraldehyde (N), and the branched, iso-butyraldehyde product (I), with the ratio of normal- to iso-(N:I) typically being greater than or equal to two. The majority of hydroformylation research, particularly within industry, has focused on optimizing the normal aldehyde selectivity while interest in selectively forming the branched aldehyde has only recently emerged. Although an industrially viable process for iso-selective chemistry has yet to be developed, recent academic results have demonstrated highly branched hydroformylation of unsubstituted linear alpha olefins. Selectively hydroformylating at the C2 carbon position of these substrates is quite challenging given that unsubstituted linear alpha olefins bear no discerning electronic or steric features.

To be considered industrially relevant, the turnover frequency of a hydroformylation catalyst system must be at least 1,000 $h^{-1}$. In addition, to avoid costly separation of linear and branched aldehydes from the product stream it would also be preferable to generate branched aldehydes in high concentration (>50%). Identifying reaction conditions conducive to achieving N:I ratios below 1.2 or even below 1.0 from hydroformylation of unsubstituted linear alpha-olefins while obtaining a reaction rate of 1,000 $h^{-1}$ or higher would therefore be desirable.

BRIEF SUMMARY OF THE INVENTION

A first embodiment of the invention concerns a process for producing aldehydes, comprising:

a) contacting a catalyst composition and a first olefin under hydroformylation conditions to prepare a catalyst ligand composition; and b) contacting a second olefin, hydrogen and carbon monoxide in the presence of said catalyst ligand composition to produce butyraldehydes and wherein the second olefin is propylene, wherein the first olefin has a longer carbon chain than propylene, and wherein said catalyst ligand composition comprises tris(3-pyridyl)phosphine, a magnesium centered tetraphenylporphyrin coordination complex and a ligand formed in situ via insertion of the first olefin into a rhodium carbonyl bond.

Another embodiment concerns a process for producing butyraldehydes, comprising:

a) contacting a catalyst composition and a first olefin under hydroformylation conditions to prepare a catalyst ligand composition; and b) contacting a second olefin, hydrogen and carbon monoxide in the presence of said catalyst ligand composition and wherein the second olefin is propylene, wherein the first olefin has a longer carbon chain than propylene, and wherein said catalyst ligand composition comprises the following structure:

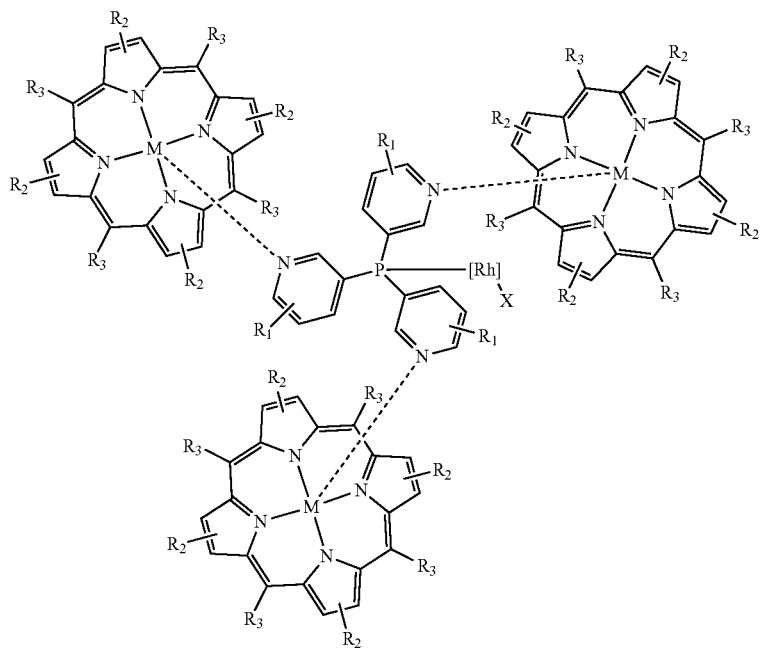

wherein M is a magnesium(II) ion;

X is a ligand formed via contacting the first olefin and the catalyst composition under hydroformylation conditions;

Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

Another embodiment concerns a catalyst composition comprising tris(3-pyridyl)phosphine, a magnesium centered tetraphenylporphyrin coordination complex and a ligand formed in situ via insertion of the first olefin into a rhodium carbonyl bond.

Still another embodiment concerns a catalyst composition comprising the following structure:

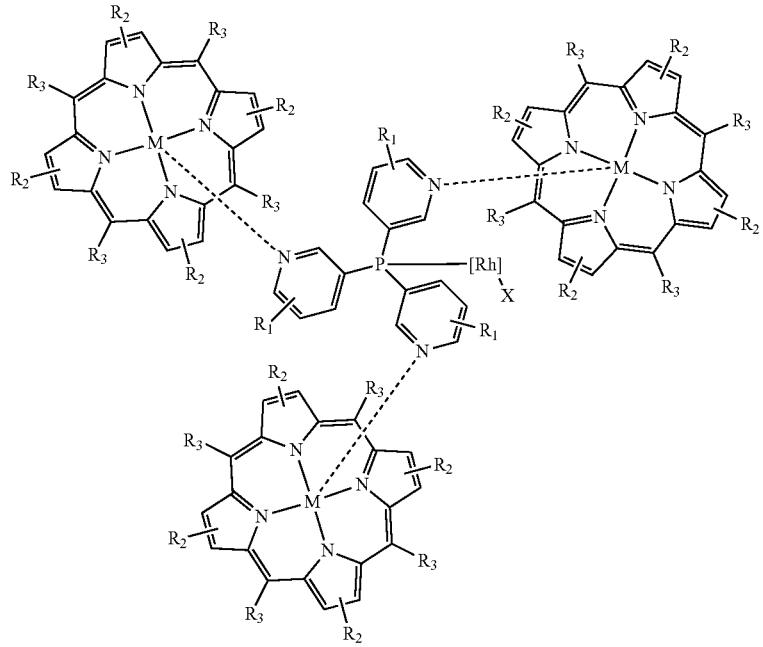

wherein M is a magnesium(II) ion;

X is a ligand formed via contacting a) an olefin and b) PPy3, TPP—Mg and a rhodium precursor under hydroformylation conditions;

Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

Yet another embodiment concerns a method for preparing a catalyst ligand composition comprising:

a) contacting a rhodium precursor with tris(3-pyridyl)phosphine and a magnesium centered tetraphenylporphyrin complex in a solvent to form a catalyst composition; and b) contacting the catalyst composition and an olefin under hydroformylation conditions to form a catalyst ligand composition.

DETAILED DESCRIPTION

Possessing the ability to produce exclusively iso-butyraldehyde at commercially relevant rates would be a significant achievement for industrial hydroformylation processes. Selective synthesis of normal-aldehydes is relatively straightforward given the advances in ligand design over the past several decades. Efforts to produce the branched isomers from unsubstituted linear alpha olefins, however, have met with little success. In other words, methods for producing normal- to iso-aldehyde (N:I) mixtures in a 1.2:1 to 25:1 ratio via rhodium catalysis are well established but industrial technologies for obtaining N:I ratios below 1.2:1 remain in their infancy. For purposes of this invention, N refers to normal (or linear) aldehydes which arise from hydroformylation of the C1 carbon of the substrate and I refers to non-linear aldehydes which arise from hydroformylation of the C2 carbon of the substrate.

According to an embodiment, the present invention concerns a catalyst ligand system that has undergone a catalyst induction period and affords branched aldehyde (iso-aldehydes) selectivity that are otherwise unattainable at elevated reaction temperature. Moreover, a turnover frequency of over 3000 $h^{-1}$ is realized when operating under these conditions. For purposes of this invention, induction period refers to a period of time of sufficient duration to allow the hydroformylation catalyst, when in the presence of a first olefin (the induction olefin) under hydroformylation conditions, to obtain a composition or molecular geometry that is selective (N:I<1.2) toward C2 hydroformylation of a second olefin, propylene (the target olefin). For the purposes of this invention, the terminology "first olefin" or "induction olefin" refers to an olefin that is used during the induction period. Moreover, the terminology "second olefin", "target olefin", "refers to propylene that reacted or contacted with carbon monoxide (CO), hydrogen ($H_2$) and the catalyst ligand system and undergoes hydroformylation.

The "Reek ligand system" is defined as a mixture of tris(3-pyridyl)phosphine (hereafter referred to as "PPy3" or "phosphine ligand" or "ligand" or "phosphine" or "pyridylphosphine") and a magnesium centered tetraphenylporphyrin coordination complex (hereafter referred to as "porphyrin complex" or "TPP—Mg" where magnesium (Mg) is the metal coordinated by the porphyrin) and a rhodium precursor. Moreover, the catalyst ligand system (or ligand system) according to the present invention is a composition comprising PPy3 and TPP—Mg and a rhodium precursor and a ligand formed in situ under hydroformylation reaction conditions via insertion of an olefin into a rhodium carbonyl bond. Hence, according to an embodiment, a catalyst ligand system (or catalyst composition) according to the present invention has the following structure:

cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment, the magnesium porphyrin complex is comprised of at least a 5, 10, 15, 20-tetraphenylporphyrin moiety bound to a magnesium(II) ion. The tetraphenylporphyrin fragment may bear functionalized phenyl rings in order to change the steric and electronic properties of the catalyst. For example, the phenyl groups of the porphyrin moiety may be substituted with one or more methyl groups, methoxy groups or nitro groups at the 2, 3, 4, 5 and 6 carbon positions of the phenyl ring. The phenyl ring may also be displaced by other aromatic cyclic hydrocarbons such as naphthalene, anthracene or partially hydrogenated cyclic aromatic compounds such as tetrahydronaphthalene or octahydroanthracene.

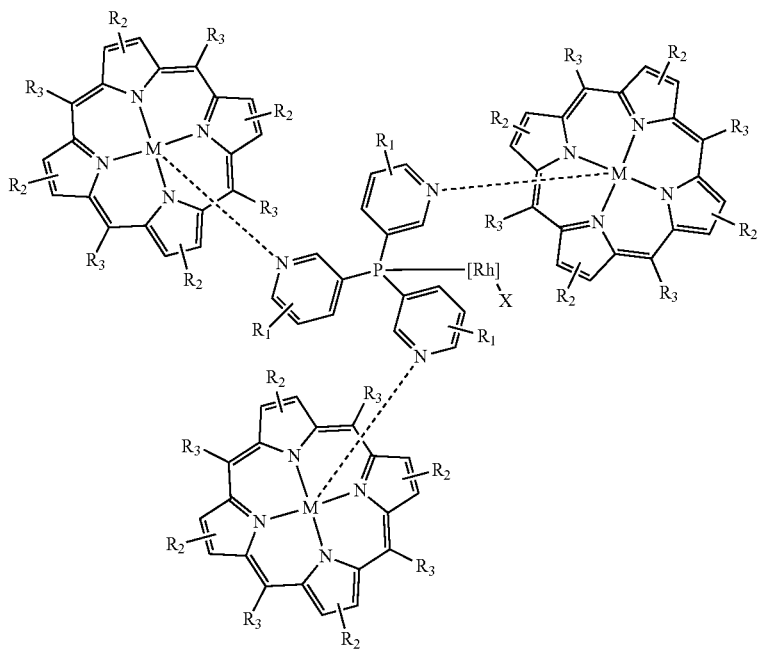

wherein M is a magnesium(II) ion; X is a ligand formed via contacting a) an olefin and b) a PPy3, TPP—Mg and a rhodium precursor under hydroformylation conditions; [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated According to an embodiment, the rhodium precursor can be any rhodium containing complex or salt bearing spectator ligands such as, but not limited to, acetylacetonatobis(cyclooctene)rhodium(I); acetylacetonatobis(ethylene)rhodium (I); acetylacetonato(1,5-cyclooctadiene)rhodium(I); bis(1,5-cycloocta-diene)rhodium(I) tetrafluoroborate; bis(1,5-cyclooctadiene)rhodium(I) trifluoromethanesulfonate; bis (norbornadiene)rhodium(I) tetrafluoroborate; chlorobis (cyclooctene) rhodium(I) dimer; chlorobis(ethylene) rhodium(I) dimer; chloro(1,5-cyclooctadiene)rhodium(I) dimer; chlorodicarbonylrhodium(I) dimer; chloronorbornadiene rhodium(I) dimer; dicarbonylacetylacetonato rhodium (I); rhodium(II) acetate dimer; rhodium(III) acetylacetonate; rhodium(III) bromide; rhodium(III) chloride; rhodium(III) iodide; rhodium(II) nitrate; rhodium(II octanoate dimer; rhodium(II) trifluoroacetate dimer; tetrarhodium dodecacarbonyl; di-rhodium tetraacetate dehydrate; rhodium(II)

acetate; rhodium(II) isobutyrate; rhodium(II) 2-ethylhexanoate; rhodium(II) benzoate and rhodium(II) octanoate. Also, rhodium carbonyl species such as $Rh_4(CO)_{12}$; $Rh_6(CO)_{16}$ and rhodium(I) acetylacetonate dicarbonyl may be suitable rhodium feeds. Additionally, rhodium organophosphine complexes such as tris(triphenylphosphine)rhodium carbonyl hydride may be used when the phosphine moieties of the complex fed are easily displaced by the tris(3-pyridyl)phosphine ligand of the present invention.

According to an embodiment, the catalyst can be prepared by combining a rhodium precursor with tris(3-pyridyl)phosphine and the magnesium centered tetraphenylporphyrin complex in a solvent. The resulting complex then undergoes an induction period wherein the complex is contacted with the induction or first olefin under hydroformylation conditions for a specified period of time followed by contacting with the target olefin, propylene. Examples of solvents include, but are not limited to, alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. The main criteria for the solvent is that it dissolves the catalyst and the second olefin and does not act as a poison to the catalyst. Examples of solvents for the production of volatile aldehydes, e.g., the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethylformamide, perfluorinated solvents such as perfluoro-kerosene, sulfolane, water, and high boiling hydrocarbon liquids as well as combinations of these solvents.

According to an embodiment, the invention concerns a process for producing butyraldehydes, such as iso-butyraldehyde, comprising contacting a catalyst composition and a first olefin under hydroformylation conditions to prepare a catalyst ligand composition, contacting propylene, hydrogen and carbon monoxide in the presence of said catalyst ligand composition, wherein the first olefin has a carbon chain of n, wherein n is 4 or greater and wherein said catalyst composition comprises tris(3-pyridyl)phosphine, a magnesium centered tetraphenylporphyrin coordination complex and a ligand formed in situ from said first olefin under hydroformylation reaction conditions.

According to another embodiment, the invention concerns a process for producing butyraldehydes, such as iso-butyraldehyde, comprising contacting a catalyst composition and a first olefin under hydroformylation conditions to prepare a catalyst ligand composition, contacting propylene, hydrogen and carbon monoxide in the presence of said catalyst ligand composition, wherein the first olefin has a carbon chain of n, wherein n is 4 or greater and wherein the catalyst composition comprises the following structure:

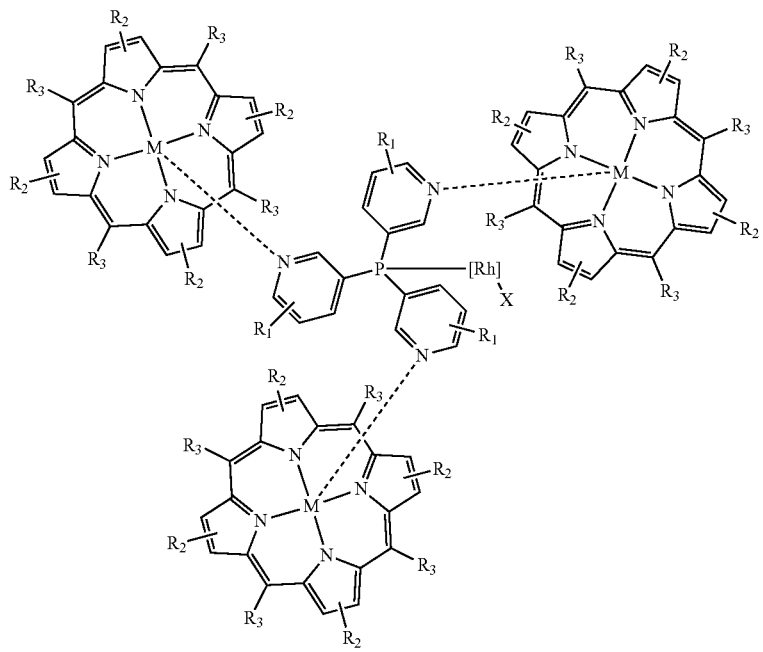

wherein M is a magnesium(II) ion; X is a ligand formed via contacting the catalyst composition and the first olefin under hydroformylation conditions via insertion of the first olefin into a rhodium carbonyl bond; [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment, the mole ratio of magnesium porphyrin complex to tris(3-pyridyl)phosphine can be from about 1000:1 to 3:1 or from about 500:1 to about 100:1 or from about 100:1 to about 50:1 or from about 50:1 to about 10:1, or from about 10:1 to about 5:1 or even from about 5:1 to about 3:1. The mole ratio of tris(3-pyridyl)phosphine ligand to rhodium can be from about 1000:1 to about 1:1 or from about 500:1 to about 100:1 or even from about 10:1 to about 1:1. The mole ratio of second olefin to rhodium can be from about 100,000:1 to about 10:1 or from about 10,000:1 to about 100:1 or even from about 5000:1 to about 1000:1.

The pressure of the reaction can be from about 345.7 bara (5000 psig) to about 1.07 bara (1 psig) or from about 69.9 bara (1000 psig) to about 7.9 bara (100 psig) or even from about 35.5 bara (500 psig) to about 14.8 bara (200 psig). The temperature during the induction period can be from about 40° C. to about 0° C. or from about 30° C. to about 10° C. or even from about 2° C. to about 15° C. The temperature of the reactor after the induction period can be from about 500° C. to about 0° C. or from about 100° C. to 50° C. or even from about 90° C. to about 70° C. The molar ratio of carbon monoxide to hydrogen can be from about 100:1 to about 50:1 or from about 50:1 to about 10:1 or from about 10:1 to about 4:1 or even from 4:1 to about 1:1. The rate of reaction, or turnover frequency, can be from about 1,000,000 h$^{-1}$ to about 100 h$^{-1}$ or from about 100,000 h$^{-1}$ to about 1000 h$^{-1}$ or even from about 10,000 h$^{-1}$ to about 3000 h$^{-1}$. The N:I ratio of normal-aldehyde product relative to iso-aldehyde product can be from about 1.2:1 to about 0.01:1 or about 1.0:1 to about 0.1:1, from about 0.6:1 to about 0.1:1 or from about 0.4:1 to about 0.25:1.

According to an embodiment, the olefins used as the induction olefins (or first olefins) can be aliphatic, including ethylenically-unsaturated, low molecular weight polymers, alicyclic, aromatic and heterocyclic mono-, di- and triolefins containing up to about 40 carbon atoms. Examples of the aliphatic olefins that may be utilized in the process include straight- and branched-chain, unsubstituted and substituted, aliphatic mono-alpha-olefins containing up to about 20 carbon atoms. Examples of the groups that may be present on the substituted mono-alpha-olefins include hydroxy; alkoxy including ethers and acetals; alkanoyloxy such as acetoxy; amino including substituted amino; carboxy; alkoxycarbonyl; carboxamide; keto; cyano; and the like. Preferred aliphatic mono-alpha-olefins have the general formulas: $H_2C=CH-R_4$ and $H_2C=CH-R_5-R_6$ wherein $R_4$ is hydrogen or straight- or branched-chain alkyl of up to about 8 carbon atoms; $R_5$ is straight- or branched-chain alkylene of up to about 18 carbon atoms; and $R_6$ is hydroxy, alkoxy of up to about 4 carbon atoms, alkanoyloxy of up to about 4 carbon atoms, carboxyl or alkoxycarbonyl of 2 to about 10 carbon atoms. Specific examples of the aliphatic mono-alpha-olefins include ethylene, propylene, 1-butene, 1-pentene, 1-hexene, 1-heptene, 1-octene, 1-nonene, 1-decene, 1-undecene, 1-dodecene, allyl alcohol and 3-acetoxy-1-propene. The aliphatic, di-olefins may contain up to about 40 carbon atoms. Preferred aliphatic, di-olefins have the general formula: $H_2C=CH-R_7-CH=CH_2$ wherein $R_7$ is straight- or branched-chain alkylene having 1 to about 18 carbon atoms. The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene. The olefin reactants which are particularly preferred comprise mono-alpha-olefins of 2 to 12 carbon atoms, especially propylene.

According to an embodiment, the porphyrin complex is comprised of at least a 5, 10, 15, 20-tetraphenylporphyrin moiety bound to a magnesium(II) ion. The tetraphenylporphyrin fragment may bear functionalized phenyl rings in order to change the steric and electronic properties of the catalyst. For example, the phenyl groups of the porphyrin moiety may be substituted with one or more methyl groups, methoxy groups or nitro groups at the 2, 3, 4, 5 and 6 carbon positions of the phenyl ring. The phenyl ring may also be displaced by other aromatic cyclic hydrocarbons such as naphthalene, anthracene or partially hydrogenated cyclic aromatic compounds such as tetrahydronaphthalene or octahydroanthracene.

Examples of suitable reactor types include, but are not limited to, stirred tank, continuous stirred tank, and tubular reactors. Any of the known hydroformylation reactor designs or configurations may be used for the hydroformylation reaction to produce the aldehyde hydroformylation product. For example, the process may be conducted in a batchwise manner in an autoclave by contacting the second olefin with syngas in the presence of the catalyst compositions described herein. It will be apparent to those skilled in the art that other reactor schemes may be used with this invention. For example, the hydroformylation reaction can be conducted in a plurality of reaction zones, in series, in parallel, or it may be conducted batchwise or continuously in a tubular plug flow reaction zone or series of such zones with recycle of unconsumed feed second olefin materials if required. The reaction steps may be carried out by the incremental addition of one of the feed second olefin materials to the other. Also, the reaction steps can be combined by the joint addition of the feed second olefin materials.

According to an embodiment of the invention the duration of the induction period can be from about 48 hours to about 1.0 minute or from about 12 hours to about 30 minutes or even from about 4 hours to about 2 hours. Moreover, following the induction period the target second olefin, propylene, can be injected into the reactor, below or above the pressure of the reactor.

EXAMPLES

This invention can be further illustrated by the following examples of preferred embodiments thereof, although it will be understood that these examples are included merely for purposes of illustration and are not intended to limit the scope of the invention unless otherwise specifically indicated.

ABBREVIATIONS

TON=Turnover number; TOF=Turnover frequency; N=normal-aldehyde; I=iso-aldehyde; acac=acetylacetonate;

TPP=Tetraphenylporphyrin (5,10,15,20-Tetraphenyl-21H, 23H-porphine); GC=Gas chromatography; S/Rh=Substrate/rhodium, L/Rh=Ligand/rhodium, TPP/L=Tetraphenylporphyrin/ligand, Mg=the magnesium(II) ion bound in the porphyrin complex; Isom.=percent isomerization.

General:

The rhodium precursor, $Rh(acac)(CO)_2$, and 1-octene were purchased from commercial suppliers. Unless otherwise stated, propylene (propene) was delivered quantitatively to the reactors by a Brooks Quantim mass flow controller. The magnesium porphyrin complex, denoted as TPP—Mg, was either purchased from commercial suppliers or prepared according to publically known procedures. The ligand used in the examples described below is tris(3-pyridyl)phosphine, prepared via a modification of publically known procedures:

A solution of 1.6 mol/L butyl lithium in hexanes (65 mL, 104 mmol) and TMEDA (14.2 mL, 94.5 mmol) was stirred in a dry flask under nitrogen for 15 minutes. The mixture was cooled to −72° C. and cold dry diethyl ether (300 mL) was added. The solution was then cooled to −115° C. 3-Bromopyridine (9.7 mL, 100.3 mmol) in 50 mL diethyl ether was added dropwise over 30 minutes keeping the temperature below −100° C. This was followed by the addition of $PCl_3$ (1.68 mL, 19.3 mmol) and after 30 minutes of stirring, a second aliquot of $PCl_3$ (0.72 mL, 1.14 mmol). The mixture was stirred for 2 hours at −100° C. and left to warm to room temperature overnight. The mixture was extracted with degassed water (4×300 mL) and the combined aqueous layers were washed with chloroform (3×400 mL). The combined organic layers were dried over $MgSO_4$ and concentrated to afford 6.65 g of a caramel-colored oil. The oil was purified by silica gel chromatography (column pre-treated with 5% triethylamine/heptane) using 0.5% MeOH/0.5% TEA/heptane to afford 2.9 g (39.6% yield) of a white solid. $^{31}P$ NMR (300 MHz, $CDCl_3$) δ −24.46. $^1H$ NMR (300 MHz, $CDCl_3$) δ 8.64 (dt, J=4.8, 1.5 Hz, 3H), 8.61-8.52 (m, 3H), 7.71-7.52 (m, 3H), 7.42-7.29 (m, 3H).

Calculations:

Percent conversion=[(amount of octene isomers+amount of products)/(amount of 1-octene fed+amount of internal octene isomers+amount of products)]×100%

Percent isomerization=[(amount of internal octene isomers+amount of 2-propylhexanal+amount of 2-ethylheptanal)/(amount of 2-methyl-octanal+amount of nonanal+amount of internal octene isomers+amount of 2-propylhexanal+amount of 2-ethylheptanal)]×100%

Percent iso-aldehyde=[(amount of iso-aldehyde)/(amount of iso-aldehyde+amount of normal-aldehyde)]×100%

Percent normal-aldehyde=[(amount of normal-aldehyde)/(amount of normal-aldehyde+amount of iso-aldehyde)]×100%

TON=[(moles of desired aldehyde produced)/(moles of $Rh(acac)(CO)_2$)]

TOF=[(moles of desired aldehyde produced)/(moles of $Rh(acac)(CO)_2$)]/hour

Examples 1-6

Effect on N:I Selectivity in 1-Octene Hydroformylation as a Function of Temperature Using the TPP—Mg Catalyst System Six separate experiments were performed for Examples 1-6, each at different reactor temperatures. In each example the hydroformylation reaction was carried out by first dissolving about 8 mg of $Rh(acac)(CO)_2$ in toluene (45 mL) followed by addition of 17.5 mg (two mole equivalents) of tris(3-pyridyl)phosphine then about 125 mg (about three mole equivalents) of the tetraphenylporphyrin magnesium complex. The solution was then degassed by argon bubbling followed by addition of about 1.37 g of 1-octene and a decane internal standard, both via syringe. The solution was then charged to an autoclave which was then pressurized and vented three times with nitrogen. Stirring was set to 1000 rpm and the reactor pressurized to 300 psig (1:1 $CO:H_2$) once the desired temperature was obtained in each case. Reactor contents were sampled at various times throughout each reaction. After eighteen hours, the autoclave was vented and the product analyzed by gas chromatography. The reaction conditions were as follows. At 19° C.: octene/Rh=407, L/Rh=2.2, TPP—Mg/L=2.8; at 25° C. octene/Rh=375, L/Rh=2.3, TPP—Mg/L=2.8; at 35° C. octene/Rh=358, L/Rh=2.1, TPP—Mg/L=3.0; at 40° C.: octene/Rh=394, L/Rh=2.2, TPP—Mg/L=2.8; at 60° C.: octene/Rh=382, L/Rh=2.1, TPP—Mg/L=2.8; at 80° C.: octene/Rh=391, L/Rh=2.1, TPP—Mg/L=2.8. The results are summarized in Tables 1 through 6. These results demonstrate that a gradual increase in iso-aldehyde concentration (i.e., the induction effect) is significant in the 19° C. experiment, giving an N:I of 0.36 (73% iso-aldehyde) after eighteen hours. As the reaction temperature is increased past 25° C. the relative amount of iso-aldehyde formed is increasingly less.

TABLE 1

| Time (h) | Substrate | T ° C. | Conv. | TON | TOF ($h^{-1}$) | N:I | iso-aldehyde | Isom. |
|---|---|---|---|---|---|---|---|---|
| 1 | 1-Octene | 19 | 0% | 0.0 | 0 | 0.00 | 0% | 0% |
| 2 | | | 0% | 1.3 | 1 | 0.00 | 0% | 0% |
| 4 | | | 3% | 11 | 5 | 0.64 | 61% | 0% |
| 6 | | | 8% | 21 | 11 | 0.67 | 60% | 0% |
| 9 | | | 20% | 48 | 16 | 0.49 | 67% | 0% |
| 12 | | | 34% | 59 | 20 | 0.42 | 70% | 0% |
| 16 | | | 54% | 79 | 20 | 0.38 | 73% | 0% |
| 18 | | | 63% | 39 | 19 | 0.36 | 73% | 0% |

TABLE 2

| Time (h) | Substrate | T ° C. | Conv. | TON | TOF (h$^{-1}$) | N:I | iso-aldehyde | Isom. |
| --- | --- | --- | --- | --- | --- | --- | --- | --- |
| 0.5 | 1-Octene | 25 | 0% | 0 | 0 | 0.00 | 0% | 0% |
| 1 | | | 0% | 0 | 0 | 0.00 | 0% | 0% |
| 2 | | | 0% | 0 | 0 | 0.00 | 0% | 0% |
| 4 | | | 3% | 12 | 6 | 0.43 | 70% | 0% |
| 6 | | | 15% | 42 | 21 | 0.58 | 63% | 0% |
| 9 | | | 32% | 66 | 22 | 0.50 | 66% | 0% |
| 12 | | | 50% | 68 | 23 | 0.48 | 68% | 0% |
| 16 | | | 58% | 28 | 7 | 0.47 | 68% | 0% |
| 18 | | | 64% | 25 | 13 | 0.46 | 68% | 0% |

TABLE 3

| Time (h) | Substrate | T ° C. | Conv. | TON | TOF (h$^{-1}$) | N:I | iso-aldehyde | Isom. |
| --- | --- | --- | --- | --- | --- | --- | --- | --- |
| 0.5 | 1-Octene | 35 | 0% | 0 | 0 | 0.00 | 0% | 0% |
| 1 | | | 6% | 20 | 40 | 0.55 | 65% | 0% |
| 2 | | | 50% | 159 | 159 | 0.71 | 59% | 0% |
| 4 | | | 80% | 110 | 55 | 0.65 | 61% | 0% |
| 6 | | | 94% | 50 | 25 | 0.65 | 61% | 0% |
| 9 | | | 97% | 10 | 3 | 0.64 | 61% | 0% |
| 12 | | | 98% | 4 | 1 | 0.64 | 61% | 0% |
| 16 | | | 98% | 0 | 0 | 0.65 | 61% | 0% |
| 18 | | | 98% | 0 | 0 | 0.65 | 61% | 0% |

TABLE 4

| Time (h) | Substrate | T ° C. | Conv. | TON | TOF (h$^{-1}$) | N:I | iso-aldehyde | Isom. |
| --- | --- | --- | --- | --- | --- | --- | --- | --- |
| 0.5 | 1-Octene | 40 | 3% | 12 | 24 | 0.00 | 0% | 0% |
| 1 | | | 4% | 5 | 10 | 0.67 | 60% | 0% |
| 2 | | | 19% | 57 | 57 | 0.80 | 56% | 0% |
| 4 | | | 69% | 198 | 99 | 0.82 | 55% | 0% |
| 6 | | | 95% | 101 | 50 | 0.82 | 55% | 0% |
| 9 | | | 98% | 14 | 5 | 0.82 | 55% | 0% |
| 12 | | | 98% | 0 | 0 | 0.82 | 55% | 0% |
| 16 | | | 98% | 0 | 0 | 0.82 | 55% | 0% |
| 18 | | | 98% | 0 | 0 | 0.82 | 55% | 0% |

TABLE 5

| Time (h) | Substrate | T ° C. | Conv. | TON | TOF (h$^{-1}$) | N:I | iso-aldehyde | Isom. |
| --- | --- | --- | --- | --- | --- | --- | --- | --- |
| 0.083 | 1-Octene | 60 | 1% | 3 | 40 | 0.67 | 60% | 0% |
| 0.17 | | | 4% | 13 | 151 | 1.00 | 50% | 0% |
| 0.5 | | | 25% | 80 | 240 | 1.06 | 49% | 0% |
| 1 | | | 77% | 198 | 395 | 1.07 | 48% | 1% |
| 2 | | | 98% | 80 | 80 | 1.05 | 49% | 1% |
| 3 | | | 98% | 2 | 2 | 1.04 | 49% | 2% |
| 5 | | | 99% | 2 | 1 | 1.02 | 49% | 2% |

TABLE 6

| Time (h) | Substrate | T ° C. | Conv. | TON | TOF (h$^{-1}$) | N:I | iso-aldehyde | Isom. |
| --- | --- | --- | --- | --- | --- | --- | --- | --- |
| 0.083 | 1-Octene | 80 | 21% | 83 | 992 | 2.11 | 32% | 3% |
| 0.17 | | | 66% | 177 | 2118 | 2.10 | 32% | 4% |
| 0.5 | | | 96% | 115 | 346 | 1.94 | 34% | 5% |
| 1 | | | 98% | 7 | 14 | 1.84 | 35% | 5% |
| 2 | | | 98% | 2 | 2 | 1.78 | 36% | 5% |
| 3 | | | 98% | 0 | 0 | 1.74 | 37% | 6% |
| 5 | | | 99% | 2 | 1 | 1.70 | 37% | 7% |

Example 7

Effect on N:I Selectivity in Propylene Hydroformylation at 19° C. as a Function of Time Using the TPP—Mg Catalyst System The hydroformylation reaction in this example was carried out as described in Example 1 except that propylene (propene) was used as substrate. The reaction conditions were as follows: S/Rh=406, L/Rh=2.2, TPP—Mg/L=3.0, 300 psig, 1:1 CO:$H_2$. Similar to the trends observed in Example 1, the results in Table 7 demonstrate that the N:I ratio decreases with time. This is further evidence of an induction period in which the catalyst is becoming more iso-selective at relatively low reaction temperature.

TABLE 7

| Time (h) | Substrate | T ° C. | Conv. | TON | TOF ($h^{-1}$) | N:I | iso-aldehyde | Isom. |
|---|---|---|---|---|---|---|---|---|
| 0.083 | Propene | 19 | 0% | 0 | 0 | 0.00 | 0% | 0% |
| 3 | | | 7% | 26 | 9 | 1.00 | 50% | 0% |
| 6 | | | 26% | 81 | 27 | 0.71 | 59% | 0% |
| 9 | | | 47% | 85 | 28 | 0.65 | 61% | 0% |
| 12 | | | 62% | 59 | 20 | 0.63 | 61% | 0% |
| 18 | | | 86% | 96 | 16 | 0.62 | 62% | 0% |

Example 8

Effect on N:I Selectivity in Propylene Hydroformylation at 80° C. as a Function of Time Using the TPP—Mg Catalyst System The hydroformylation reaction in this example was carried out as described in Example 7 except that the reactor temperature was set to 80° C. prior to the pressurization step. The reaction conditions were as follows: S/Rh=406, L/Rh=2.1, TPP—Mg/L=3.0, 300 psig, 1:1 CO:$H_2$. The results summarized in Table 8 show that the N:I ratio quickly levels out at 1.44 (41% iso-butyraldehyde) at this relatively high temperature.

TABLE 8

| Time (h) | Substrate | T ° C. | Conv. | TON | TOF ($h^{-1}$) | N:I | iso-aldehyde | Isom. |
|---|---|---|---|---|---|---|---|---|
| 0.083 | Propene | 80 | 36% | 147 | 1760 | 1.57 | 39% | 0% |
| 0.17 | | | 97% | 247 | 593 | 1.44 | 41% | 0% |
| 0.5 | | | 100% | 11 | 11 | 1.44 | 41% | 0% |

Example 9

Effect on N:I Selectivity in Propylene Hydroformylation by Exploiting the Induction Effect Imparted by Initial 1-Octene Hydroformylation at 19° C. then Propylene Hydroformylation at 80° C.

The hydroformylation reaction in this example was carried out as described in Example 1 except that initially 1-octene was used as the first olefin for the first 48 hours at 19° C. The autoclave was then vented down to 50 psig, then propylene was injected and the autoclave immediately heated to 80° C. The reaction conditions were as follows: octene/Rh=741, propene/Rh=802, L/Rh=2.2, TPP—Mg/L=2.7, 300 psig, 1:1 CO:$H_2$. Similar to the trend observed in Example 1, the results in Table 9 demonstrate that the N:I ratio from 1-octene hydroformylation decreases with time. More intriguing, however, is the fact that the N:I ratio from propylene hydroformylation after the 48 hour induction period is about 1.0 (50% iso-butyraldehyde). As a consequence of operating at 80° C., the initial TOF in the propylene conversion is more than 3000 $h^{-1}$.

TABLE 9

| Time (h) | Substrate | T °C. | Conv. | TON | TOF (h$^{-1}$) | N:I | iso-aldehyde | Isom. |
|---|---|---|---|---|---|---|---|---|
| 0.83 | 1-Octene | 19 | 0% | 0 | 0 | 0.00 | 0% | 0% |
| 6 | | | 7% | 48 | 8 | 0.45 | 69% | 0% |
| 12 | | | 22% | 113 | 19 | 0.33 | 75% | 0% |
| 18 | | | 41% | 140 | 23 | 0.30 | 77% | 0% |
| 24 | | | 52% | 83 | 14 | 0.30 | 77% | 0% |
| 30 | | | 64% | 87 | 15 | 0.31 | 77% | 0% |
| 36 | | | 73% | 67 | 11 | 0.31 | 77% | 0% |
| 42 | | | 79% | 45 | 8 | 0.30 | 77% | 0% |
| 48 | | | 84% | 40 | 7 | 0.30 | 77% | 0% |
| 0.083 | Propene | 80 | 34% | 272 | 3263 | 1.08 | 48% | 0% |
| 0.63 | | | 62% | 222 | 404 | 1.01 | 50% | 0% |
| 1.5 | | | 64% | 31 | 61 | 0.94 | 51% | 0% |
| 2 | | | 76% | 97 | 194 | 0.93 | 52% | 0% |

TABLE 10

Summary of the results from examples 8 and 9

| Example | Octene stage (inductive) | | Propylene stage | | Propylene conversion | N:I |
|---|---|---|---|---|---|---|
| | H2/CO | hour | H2/CO | hour | | |
| 8 | | | 1:1 | 0.5 | 100% | 1.44 |
| 9 | 1:1 | 48 | 1:1 | 2 | 76% | 0.93 |

Table 10 indicates that without the induction step of the octene stage, propylene was converted with a 1.44 N:I ratio. However, with the induction step of the octene stage, propylene was converted with a 0.93 N:I ratio.

heated to 80° C. then pressurized to 300 psig with 1:1 CO:H$_2$. The reaction conditions were as follows: octene/Rh=406, propene/Rh=152, L/Rh=2.2, TPP—Mg/L=2.7, 300 psig, 1:1 CO:H$_2$. The results summarized in Table 11 show that the N:I selectivity from both the propylene and 1-octene hydroformylations are nearly identical to those observed in the control experiments (Examples 7 and 6, respectively). In other words, use of propylene during the catalyst induction period at 19° C. does not necessarily convert the rhodium catalyst to a thermally robust iso-selective species. The internal octene isomers formed in this reaction are the likely source of increasing branched aldehyde product, as evidenced by the high degree of isomerization shown in Table 11.

TABLE 11

| Time (h) | Substrate | T °C. | Conv. | TON | TOF (h$^{-1}$) | N:I | iso-aldehyde | Isom. |
|---|---|---|---|---|---|---|---|---|
| 0.83 | Propene | 19 | 0% | 0 | 0 | 0.00 | 0% | 0% |
| 6 | | | 40% | 162 | 27 | 0.70 | 59% | 0% |
| 12 | | | 73% | 135 | 22 | 0.63 | 61% | 0% |
| 18 | | | 91% | 72 | 12 | 0.62 | 62% | 0% |
| 24 | | | 94% | 14 | 2 | 0.61 | 62% | 0% |
| 30 | | | 95% | 3 | 0 | 0.62 | 62% | 0% |
| 36 | | | 95% | 0 | 0 | 0.62 | 62% | 0% |
| 42 | | | 95% | 0 | 0 | 0.61 | 62% | 0% |
| 48 | | | 95% | 0 | 0 | 0.61 | 62% | 0% |
| 0.083 | 1-Octene | 80 | 29% | 45 | 539 | 2.29 | 30% | 16% |
| 0.5 | | | 90% | 93 | 222 | 2.06 | 33% | 11% |
| 1 | | | 97% | 11 | 21 | 1.92 | 34% | 13% |
| 1.5 | | | 97% | 0 | 0 | 1.83 | 35% | 12% |
| 2 | | | 97% | 0 | 0 | 1.78 | 36% | 13% |

Example 11

Effect on N:I Selectivity in 1-Octene Hydroformylation by Using Propylene as the Induction Olefin at 19° C. then Octene Hydroformylation at 80° C.

The hydroformylation reaction in this example was carried out as described in Example 8 except that initially propylene was used as the first olefin for the first 48 hours at 19° C. The autoclave was then vented down to 50 psig, then the second olefin, 1-octene, was injected and the autoclave immediately Example 12

Effect on N:I Selectivity in Propylene Hydroformylation by Exploiting the Induction Effect Imparted by Initial Propylene Hydroformylation at 19° C. then Heating to 80° C.

The hydroformylation reaction in this example was carried out as described in Example 11 except that octene addition was omitted prior to the heating step. Initially, the reactor was maintained at 19° C. for 48 hours. A second charge of propylene was added then the autoclave was heated to 80° C. and sampling continued. The reaction conditions were as follows: propene/Rh=401 (at 19° C.), =802 (at 80° C.), L/Rh=2.1, TPP—Mg/L=3.0, 300 psig, 1:1 CO:H$_2$. Similar to the trend observed in Example 11, the results in Table 12 demonstrate that the N:I ratio from propylene hydroformylation decreases with time, ending up at 0.67 (60% iso-butyraldehyde) after eighteen hours. Unlike Example 9, however, the N:I ratio quickly surpasses 1.0 upon heating the reactor to 80° C. This indicates that the iso-selective catalyst produced during the induction period with propylene may not be as dominant or thermally robust at 80° C. as the catalyst formed from an induction period employing 1-octene.

Examples 11-13 indicate that using a first olefin, a compound with a shorter or same carbon number chain than the second olefin in the inductive stage, does not achieve the desired N:I rate of below 1.2:1. In other words, to achieve the desired N:I rate of below 1.2:1, the first olefin has to be a compound with a longer carbon chain than the second olefin.

The invention has been described in detail with particular reference to preferred embodiments thereof, but it will be understood that variations and modifications can be effected within the spirit and scope of the invention.

TABLE 12

| Time (h) | Substrate | T ° C. | Conv. | TON | TOF (h$^{-1}$) | N:I | iso-aldehyde | Isom. |
|---|---|---|---|---|---|---|---|---|
| 0.083 | Propene | 19 | 0% | 0 | 0 | 0.00 | 0% | 0% |
| 3 | | | 0% | 0 | 0 | 0.00 | 0% | 0% |
| 6 | | | 0% | 0 | 0 | 0.00 | 0% | 0% |
| 9 | | | 4% | 16 | 5 | 1.00 | 50% | 0% |
| 12 | | | 10% | 23 | 8 | 0.88 | 53% | 0% |
| 15 | | | 28% | 74 | 25 | 0.70 | 59% | 0% |
| 18 | | | 57% | 116 | 39 | 0.67 | 60% | 0% |
| 0.083 | | 80 | 79% | 405 | 4866 | 1.15 | 46% | 0% |
| 0.5 | | | 96% | 136 | 327 | 1.25 | 44% | 0% |
| 1 | | | 99% | 26 | 52 | 1.28 | 44% | 0% |
| 1.5 | | | 100% | 2 | 3 | 1.28 | 44% | 0% |

Example 13

Effect on N:I Selectivity in 1-Octene Hydroformylation by Exploiting the Induction Effect Imparted by Initial 1-Octene Hydroformylation at 19° C. then Heating to 80° C.

The hydroformylation reaction in this example was carried out as described in Example 9 except that propylene addition was omitted prior to the heating step. Initially, the reactor was maintained at 19° C. for 18 hours then the autoclave was heated to 80° C. and sampling continued. The reaction conditions were as follows: 1-octene/Rh=735, L/Rh=2.2, TPP—Mg/L=2.7, 300 psig, 1:1 CO:H$_2$. Similar to the trend observed in Example 9, the results in Table 13 demonstrate that the N:I ratio from 1-octene hydroformylation decreases with time, ending up at 0.28 (78% iso-butyraldehyde) after eighteen hours. However, 1-octene, instead of propylene, was the second/target olefin in this example, and the N:I ratio quickly approached 0.7 upon heating the reactor to 80° C. Moreover, the octene isomerization rate was approximately 10%. This indicates that the induction effect is not operative on a longer chain olefin such as 1-octene at a rate higher than the rate of isomerization.

We claim:

1. A process for producing aldehydes, comprising:
   a) contacting a catalyst composition and a first olefin under hydroformylation conditions to prepare a catalyst ligand composition; and
   b) contacting a second olefin, hydrogen and carbon monoxide in the presence of said catalyst ligand composition to produce aldehydes wherein the second olefin is propylene,
   wherein the first olefin has a longer carbon chain than the second olefin, and
   wherein said catalyst ligand composition comprises tris(3-pyridyl)phosphine, a magnesium centered tetraphenylporphyrin coordination complex and a ligand formed in situ via insertion of the first olefin into a rhodium carbonyl bond.

2. A process according to claim 1, wherein the aldehydes are produced in an N:I ratio of from about 1.2:1 to about 0.01:1.

3. A process according to claim 2, wherein the N:I ratio is from about 1.0:1 to about 0.1:1.

TABLE 13

| Time (h) | Substrate | T ° C. | Conv. | TON | TOF (h$^{-1}$) | N:I | iso-aldehyde | Isom. |
|---|---|---|---|---|---|---|---|---|
| 0.083 | 1-Octene | 19 | 0% | 0.0 | 0.0 | 0.00 | 0% | 0% |
| 3 | | | 3% | 20 | 7.0 | 0.38 | 72% | 0% |
| 6 | | | 12% | 70 | 23 | 0.31 | 77% | 0% |
| 9 | | | 20% | 56 | 19 | 0.29 | 77% | 0% |
| 12 | | | 27% | 55 | 18 | 0.28 | 78% | 0% |
| 15 | | | 34% | 49 | 16 | 0.28 | 78% | 0% |
| 18 | | | 41% | 49 | 16 | 0.28 | 78% | 0% |
| 0.083 | | 80 | 60% | 138 | 1661 | 0.47 | 68% | 3% |
| 0.25 | | | 87% | 204 | 1222 | 0.67 | 60% | 4% |
| 0.5 | | | 96% | 67 | 269 | 0.71 | 59% | 10% |
| 1 | | | 98% | 11 | 22 | 0.69 | 59% | 8% |

4. A process according to claim 2, wherein the N:I ratio is from about 0.6:1 to about 0.1:1.

5. The process according to claim 3, wherein the N:I ratio is from about 0.4:1 to about 0.25:1.

6. The process according to claim 1, wherein the first olefin is a butene, a pentene, a hexene, a heptene, an octene, a nonene, a decene, an undecene, or a dodecene.

7. The process according to claim 1, wherein a mole ratio of magnesium centered tetraphenylporphyrin coordination complex to tris(3-pyridyl)phosphine is from about 1000:1 to 3:1.

8. The process according to claim 1, wherein a mole ratio of tris(3-pyridyl)phosphine ligand to rhodium precursor is from about 1000:1 to about 1:1.

9. The process according to claim 1, wherein a mole ratio of olefin to rhodium precursor is from about 100,000:1 to about 10:1.

10. The process according to claim 1, wherein a ratio of carbon monoxide to hydrogen can be from about 10:1 to about 0.1:1.

11. The process according to claim 1, wherein the aldehydes are butyraldehydes and iso-butyraldehyde.

12. A process for producing aldehydes, comprising:
a) contacting a catalyst composition and a first olefin under hydroformylation conditions to prepare a catalyst ligand composition; and
b) contacting a second olefin, hydrogen and carbon monoxide in the presence of said catalyst ligand composition wherein the second olefin is propylene,
wherein the first olefin has a longer carbon chain than propylene, and
wherein said catalyst ligand composition comprises the following structure:

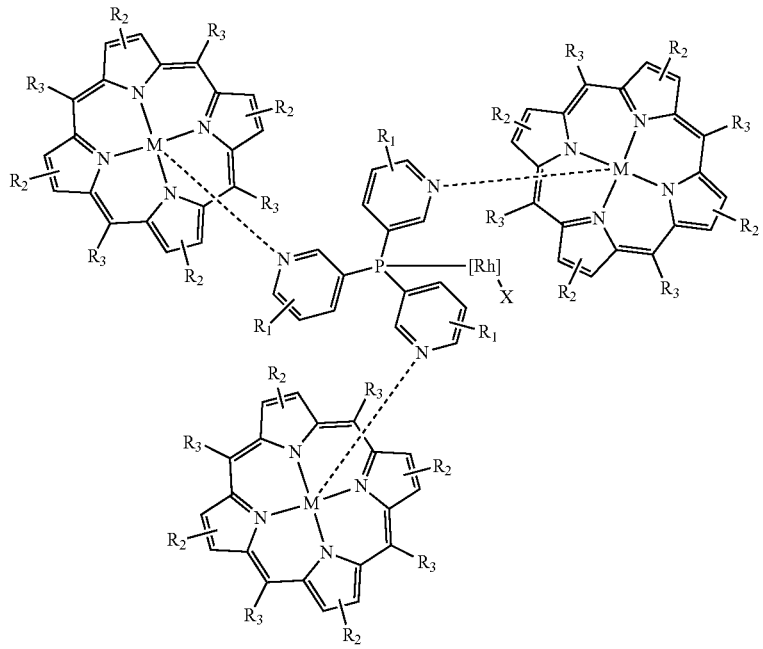

wherein M is a magnesium(II) ion;
X is a ligand formed via contacting the first olefin and catalyst composition under hydroformylation conditions
Rh is a rhodium(I), rhodium(II) or rhodium(III) metal center;
$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;
$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and
$R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

13. A catalyst composition comprising tris(3-pyridyl)phosphine, a magnesium centered tetraphenylporphyrin coordination complex and a ligand formed in situ via insertion of an olefin into a rhodium carbonyl bond.

14. A catalyst composition comprising the following structure:

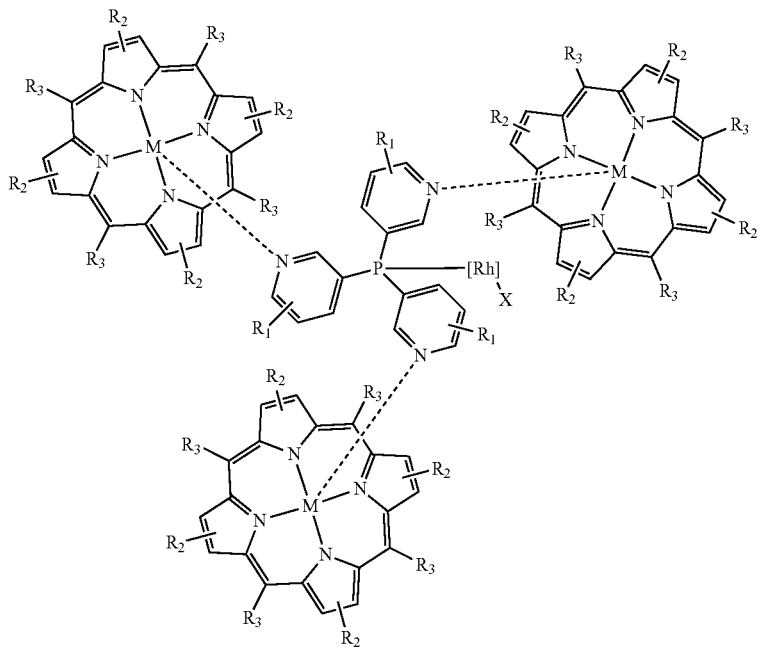

wherein M is a magnesium(II) ion;

X is a ligand formed via contacting a) an olefin and b) PPy3, TPP—Mg and a rhodium precursor under hydroformylation conditions;

Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

15. A method for preparing a catalyst ligand composition comprising:
   a) contacting a rhodium precursor with tris(3-pyridyl) phosphine and a magnesium centered tetraphenylporphyrin complex in a solvent to form a catalyst composition; and
   b) contacting the catalyst composition and an olefin under hydroformylation conditions to form a catalyst ligand composition.

16. The method according to claim 14, wherein the solvent is a benzene, a toluene, a xylene, a pentane, a hexane, a heptane, an octane, a nonane, an ethyl acetate, a dichloromethane, a diethyl ether or mixtures thereof.

* * * * *